United States Patent
Zhang (10) Patent No.: US 10,016,138 B2
(45) Date of Patent: Jul. 10, 2018

(54) METHOD AND DEVICE FOR LONG-TERM MONITORING OF ARTERIAL VASCULAR STIFFNESS AND VASCULAR CALCIFICATION OF A PATIENT

(71) Applicant: Fresenius Medical Care Deutschland GmbH, Bad Homburg (DE)

(72) Inventor: Wei Zhang, Niederwerrn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1133 days.

(21) Appl. No.: 13/860,666

(22) Filed: Apr. 11, 2013

(65) Prior Publication Data

US 2013/0274620 A1 Oct. 17, 2013

Related U.S. Application Data

(60) Provisional application No. 61/622,667, filed on Apr. 11, 2012.

(30) Foreign Application Priority Data

Apr. 11, 2012 (DE) ........................ 10 2012 007 081

(51) Int. Cl.
  *A61B 5/02* (2006.01)
  *A61B 5/021* (2006.01)
  *A61B 5/022* (2006.01)
(52) U.S. Cl.
  CPC ...... *A61B 5/02007* (2013.01); *A61B 5/02125* (2013.01); *A61B 5/02225* (2013.01)
(58) Field of Classification Search
  None
  See application file for complete search history.

(56) References Cited

U.S. PATENT DOCUMENTS 6,331,162 B1 * 12/2001 Mitchell ............ A61B 5/02125
  600/485
6,511,436 B1 * 1/2003 Asmar ................... A61B 5/021
  600/481

(Continued)

FOREIGN PATENT DOCUMENTS

DE   10 2006 010813    9/2007
WO   WO 98/55021     12/1998
WO   WO 2005/077265   8/2005

OTHER PUBLICATIONS

Styczynski, Grzegorz, et al. "Descending aortic Doppler flow pattern in patients with proximal peripheral artery disease." The American journal of cardiology 103.12 (2009): 1774-1776.*

(Continued)

*Primary Examiner* — Jacqueline Cheng
*Assistant Examiner* — Jairo Portillo
(74) *Attorney, Agent, or Firm* — Jacobson Holman, PLLC.

(57) ABSTRACT

The present invention proposes a method and a device for long-term monitoring of the arterial vascular stiffness and vascular calcification on a particular patient, wherein a characteristic variable for the arterial vascular stiffness is determined exclusively from the shape and/or the characteristic of at least one pressure pulse wave caused by a cardiac contraction as a function of time and is stored as a time series for the particular patient. In particularly preferred embodiments, the characteristic variable is represented as a trend and serves the physician as a basis for long-term monitoring of the arterial vascular stiffness.

14 Claims, 5 Drawing Sheets

(56) References Cited

U.S. PATENT DOCUMENTS

| | | | |
|---|---|---|---|
| 6,736,789 B1* | 5/2004 | Spickermann | A61B 5/02125 128/DIG. 3 |
| 7,264,594 B2 | 9/2007 | Shimazu et al. | |
| 2002/0120201 A1 | 8/2002 | Chio | |
| 2003/0004420 A1* | 1/2003 | Narimatsu | A61B 5/02 600/485 |
| 2003/0083580 A1* | 5/2003 | Tampo | A61B 5/021 600/490 |
| 2004/0019284 A1* | 1/2004 | Kawaguchi | A61B 5/02125 600/485 |
| 2004/0162035 A1* | 8/2004 | Petersen | A61B 5/02055 455/90.1 |
| 2006/0224073 A1* | 10/2006 | Lin | A61B 5/02007 600/513 |
| 2006/0247538 A1 | 11/2006 | Davis | |
| 2007/0004985 A1 | 1/2007 | Suzuki et al. | |
| 2008/0212032 A1* | 9/2008 | Seiller | G09B 19/0038 351/246 |
| 2009/0050544 A1 | 2/2009 | Zhang | |
| 2009/0162820 A1* | 6/2009 | Tada | A61B 8/08 434/272 |
| 2010/0016735 A1* | 1/2010 | Harpas | A61B 5/02125 600/485 |
| 2010/0113891 A1* | 5/2010 | Barrett | A61B 5/14535 600/301 |

OTHER PUBLICATIONS

Parati et al. "Evaluating aortic stiffness through an arm cuff oscillometric device: is validation against invasive measurements enough?" Journal of Hypertension, vol. 28, No. 10, Oct. 2010, pp. 2003-2006.

Huybrechts et al. "Carotid to femoral pulse wave velocity: a comparison of real travelled aortic path lengths determined by MRI and superficial measurement." Journal of Hypertension, vol. 29, No. 8, Aug. 2011, pp. 1577-1582.

Yamagishi et al. "A Comparative Study of Arterial Stiffness Indices in Outpatients." In. 37$^{th}$ Niigata Meeting on Hypertension, Niigata University, Feb. 7, 2004.

* cited by examiner

METHOD AND DEVICE FOR LONG-TERM MONITORING OF ARTERIAL VASCULAR STIFFNESS AND VASCULAR CALCIFICATION OF A PATIENT

FIELD OF THE INVENTION

The invention relates to the field of monitoring the cardiovascular stability of patients, in particular patients who must regularly rely on an extracorporeal blood treatment. According to the invention, a novel method and a novel device for determining at least one characteristic variable for arterial vascular stiffness and vascular calcification during a plurality of blood treatment sessions and storing at least one value of the characteristic variable per blood treatment session to establish a long-term trend of the at least one characteristic variable are proposed. The novel method and the novel device also allow continuous measurement of blood pressure.

STATE OF THE ART

Various types of blood treatment devices are known. The known blood treatment devices include devices for hemodialysis, hemofiltration and hemodiafiltration, for example. During an extracorporeal blood treatment, the blood flows in an extracorporeal blood circulation through a blood treatment unit, e.g., a dialyzer. Monitoring of the cardiovascular stability of the patient's bloodstream during an extracorporeal blood treatment is a constant challenge for the staff at a dialysis clinic. One important aspect here is the earliest possible detection of short-term hypotensive episodes during an extracorporeal blood treatment session. Various methods and devices for monitoring the blood pressure and pulse rate of the patient during a blood treatment session are known from the state of the art.

The applicant, Fresenius Medical Deutschland GmbH, distributes a module under the name "Blood Pressure Monitor" (BPM) for performing a non-invasive oscillometric measurement of the systolic blood pressure, the diastolic blood pressure, the mean arterial blood pressure (MAP) and also for measuring the heart rate. In addition to measurements initiated manually, automatic measurements at predetermined intervals during a blood treatment session are also possible with the BPM module. For example, the BPM module is used as a component of the hemodialysis machines of the applicant Fresenius Medical Care Deutschland GmbH from the model series 4008 and 5008, where the measurement results can be recorded on the electronic data media connected to the hemodialysis machine. Such a method and such a device are described in the specification DE 10 2006 010 813 A1 from the present applicant, for example. However, the BPM module requires that a traditional pressure-measuring cuff be applied to the patient's upper arm, so that in practice, measurements are performed discontinuously at intervals of approximately one hour. The BPM module in the known embodiment using a traditional sphygmomanometer cuff is therefore less suitable for continuous monitoring to allow the earliest possible detection of short-term hypotensive episodes during an extracorporeal blood treatment session.

Another known method of the aforementioned generic type for continuous monitoring of blood pressure is based on the relationship between the pulse wave velocity (PWV) and/or the pulse transit time (PTT) and the blood pressure. In these known methods, assumptions are made with regard to the relationship between the pulse wave velocity in the arteries and the arterial vascular stiffness. The calculations of the blood pressure are based in particular on the assumption that the arterial vascular stiffness can be considered to be constant during the measurement time. Then the measured variables PWV and/or PTT are determined continuously and simultaneously by means of a photoplethysmogram (PPG) and electrocardiogram (ECG). In such methods, it is necessary to apply additional PPG probes and ECG probes to the patient using the corresponding measurement cables.

It is known that a patient's acceptance of a monitoring device drops with the increasing number of cables and sensors attached to the patient. For the acceptance of monitoring devices by dialysis patients, it would be desirable for the dialysis patients not to have to accept any further restrictions, such as freedom of movement, which is limited anyway, in addition to the already substantial restrictions due to the extracorporeal blood circulation. Methods based on the use of a plurality of additional sensors on the patient such as ECG probes and cables and PPG probes and cables are therefore a disadvantage in practice. Furthermore, the effort for the staff at the dialysis clinic increases with an increase in the number of cables and sensors attached to the patient and not least of all the devices themselves constitute a cost factor.

Measurements of the aforementioned type are based on the observation period of one blood treatment session, for example, approximately four to five hours, and serve primarily to ensure patient safety during the individual dialysis treatment. The measurement data are not analyzed further thereafter and are deleted because the monitoring task is concluded at the end of the treatment.

In a long-term observation period including numerous blood treatment sessions, the attending physician must take into account some other health-relevant parameters. For example, the risk assessment of possible pathological vascular changes, for example, arterial vascular calcification and/or arteriosclerosis can have an influence on the ongoing medication taken by a dialysis patient. Selected characteristic parameters of the instantaneous status of stiffness and/or elasticity of the arterial vascular system can be ascertained by the attending physician, for example, using the method described in the specification WO 2005/077265 A1 by the applicant Illyes and Beres. For example, the so-called "Augmentation Index (AIx)"; and the so-called "Ejection Duration Index (ED)" are determined by means of this method as characteristic parameters of the stiffness and/or elasticity of the arterial vascular system. A corresponding medical measuring and computing unit is distributed under the brand name Arteriograph by Arteriomed GmbH, Germany. Furthermore, the specification WO 2005/077265 A1 describes a method for oscillometric blood pressure measurement on the basis of a conventional sphygmometer cuff on the patient's upper arm.

THE PRESENT INVENTION

Objects of the Present Invention

One object of the present invention is to provide an additional method and an additional measuring and computing unit for monitoring the cardiovascular stability of a patient, in particular for continuous automatic monitoring of the blood pressure and for determining at least characteristic parameter for characterizing the arterial vascular stiffness of a certain patient. In the present invention, a characteristic parameter is understood to be a parameter which describes the vascular stiffness of a certain patient or the change therein. The characteristic parameter may be an amount expressed with a dimension or a dimensionless amount. A patient's vascular stiffness may change due to vascular calcification.

Another object of the present invention is to provide a method and a measuring and computing unit for long-term monitoring of arterial vascular stiffness of a certain patient.

Another object of the present invention is to provide an extracorporeal blood treatment device having an integrated measuring and computing unit which is configured so that long-term monitoring of the arterial vascular stiffness of a certain patient is made possible by using it.

Another object of the present invention is to provide a measuring and computing unit for long-term monitoring of the arterial vascular stiffness of a patient without requiring any additional sensor system besides the traditional non-invasive blood pressure measurement on the patient.

Another object of the present invention is to provide a method and a measuring and computing unit for monitoring the cardiovascular stability of a patient, this method and unit also necessitating long-term monitoring of the arterial vascular stiffness of the certain patient in addition to short-term continuous automatic monitoring of the blood pressure during a blood treatment session, without requiring additional equipment to do so.

Another object of the present invention is to provide an especially inexpensive method and measuring and computing unit for long-term monitoring of the arterial vascular stiffness of a certain patient.

Another object of the present invention is to provide an especially user-friendly method and measuring and computing unit for long-term monitoring of the arterial vascular stiffness of a certain patient.

One object of the present invention is to provide a method and a measuring and computing unit for long-term monitoring of the arterial vascular stiffness of a certain patient which can be implemented by an additional hardware component, e.g., an additional electronic circuit board and a software update in the known module for blood pressure monitoring (BPM) of the applicant Fresenius Medical Care Deutschland GmbH.

These problems are solved according to the invention features and advantageous embodiments described below. The advantages of the method according to the described invention can be achieved with the described invenion device for non-invasive, artery related measurement and the described invention device for extracorporeal blood treatment without being diminished. In certain embodiments, the advantages of the method according to the invention can be achieved with the described computer program product invention without being diminished.

According to the teaching of the invention, these problems are solved by an oscillometric analysis of at least one pressure pulse wave caused by a cardiac contraction as a function of time. The characteristic variable that is sought for the arterial vascular stiffness of a particular patient can be determined from the shape and/or the curve of at least one pressure pulse wave caused by a cardiac contraction of the particular patient as a function of time, provided that length of the descending aorta of the particular patient is constant.

Measurement of the at least one pressure pulse wave caused by a cardiac contraction is especially preferably performed on the patient by means of a pressure sensor. According to this invention, it is also possible to measure and evaluate the so-called heart volume pulse by means of an optical sensor or to measure and evaluate the so-called blood flow pulse by means of an ultrasonic measurement according to this invention.

In particular the shape and/or the curve of at least one pressure pulse wave caused by a cardiac contraction of the particular patient as a function of time according to this invention may include the determination of the point in time of the systolic maximum and the determination of the point in time of another local pulse event occurring chronologically after the systolic maximum, said pulse event occurring because of the pressure pulse wave of the selected heart beat reflected on the patient's aortic bifurcation. The local pulse event occurring chronologically after the systolic maximum may be a local maximum or a local turning point. The pulse wave transit time in the patient's descending aorta can be calculated as a measure of the arterial vascular stiffness from the difference between the point in time of the local pulse event caused by the pressure pulse wave of the selected heart beat reflected on the patient's aortic bifurcation and the point in time of the systolic maximum of the selected heartbeat. If the length of the descending aorta of the particular patient is known, the pulse wave velocity can be calculated as another measure of the arterial vascular stiffness.

Within the context of further development of the aforementioned blood pressure monitor BPM by the applicant, Fresenius Medical Care Deutschland GmbH, with a piezoelectric measurement of the blood pressure on the patient's wrist and corresponding studies by the applicant on a population of test subjects, it has been discovered that by merely analyzing the characteristic of at least one pressure pulse wave caused by a cardiac contraction as a function of time, thus using comparatively simple means, not only is a reliable monitoring of blood pressure during a single blood treatment session possible but, in addition, it is also possible to reliably infer a possible long-term change in the arterial vascular stiffness if the observation period is expanded to a plurality of blood treatment sessions. Arterial vascular calcification can be inferred from the characteristic variable for the arterial vascular stiffness.

To detect a change in the arterial vascular stiffness of a particular patient, the trend in the pulse wave transit time can be analyzed. According to the invention, the length of the descending aorta of the particular patient is assumed to be constant, without having to know the amount. Even the trend in the pulse wave transit time of the particular patient can provide a hint of whether the trend in the arterial vascular stiffness is constant, increasing or decreasing. If in addition a hint is to be obtained as to whether the arterial vascular stiffness of the particular patient corresponds to the age of the particular patient or is increased or even critically increased, this is possible only with knowledge of the length of the descending aorta of the particular patient, so that a comparison with empirical values is possible.

For the same patient, the pulse wave velocity determined is inversely proportional to the pulse wave transit time, assuming the length of the descending aorta of the same patient to be constant.

The pulse wave velocity of the descending aorta of the particular patient is especially preferably suitable as the characteristic variable for characterizing the arterial vascular stiffness; according to the invention, pulse wave velocity can be determined from the shape and/or the characteristic of at least one pressure pulse wave caused by a cardiac contraction as a function of time and as a function of the length of the patient's descending aorta, this length being determined for the particular patient. The comparison of the measured pulse wave velocity with empirical values can provide a hint of whether the arterial vascular stiffness of the particular patient corresponds to the age of the particular patient or is increased or is even critically elevated.

The length of the descending aorta must be determined individually for each patient; in other words, the length of the descending aorta may be different with different patients. The length of the descending aorta of a patient may be determined easily by a non-invasive method with sufficient accuracy according to the invention.

The present invention reverses the traditional approach, which starts from a constant vascular stiffness during the observation period and makes the new assumption that in the observation period, which was extended to a plurality of blood treatment sessions, only the length of the descending aorta may be considered as constant for a given patient but the arterial vascular stiffness may be variable. This opens up the approach of calculating characteristic values, which are comparable to one another and are detected in successive intervals over a long period of time for the arterial vascular stiffness of a patient and determining trends, such that the same value for the length of the descending aorta is always used as the basis for the recurring calculations of the characteristic variable of the arterial vascular stiffness.

The characteristic of at least one pressure pulse wave caused by a cardiac contraction as a function of time can be especially advantageous according to the present invention by piezoelectric measurement of the blood pressure on the patient's wrist or by means of a traditional by means of a traditional sphygmomanometer cuff on the patient's upper arm.

The method according to the invention and the device according to the invention enable the attending physician to especially advantageously perform long-term monitoring of the arterial vascular stiffness for risk assessment of patients, who must rely on an extracorporeal blood treatment, because in such patients, the blood pressure can be measured continuously during the regular blood treatment sessions, thereby generating measured data which may also be analyzed according to the invention. The extent of the vascular calcification can be inferred from the characteristic variable of the arterial vascular stiffness.

The device according to the invention and the method according to the invention can provide the attending physician with important information for the patient-specific optimization of the extracorporeal blood treatment, for example, for a targeted adjustment of the Ca concentration of the dialysis fluids used. The quality of the extracorporeal blood treatment therapy can therefore be further improved by the present invention.

In addition, the present invention and the present method provide the attending physician with important information for monitoring and optimizing a medicinal therapy accompanying the blood treatment, e.g., against hypocalcemia, in particular in administration of vitamin D preparations for treating a calcitriol deficiency.

On the whole, patient safety can be further improved permanently through the use of the present invention.

As a rule, a hemodialysis patient with ESRD (end stage renal disease) will undergo a hemodialysis treatment for several hours three times a week on the average over a period of a few or many years. In of the present invention, the phrase "a long period of time" is understood to be a period of a few weeks, several weeks or many weeks, months or years, for example. With regard to the application of the present invention in hemodialysis patients, a long period of time is understood to include essentially a plurality of blood treatment sessions.

In many embodiments of the present invention, the at least one characteristic variable for characterizing the arterial vascular stiffness can be determined during a plurality of blood treatment sessions and the value of the at least one characteristic value for characterizing the arterial vascular stiffness can be stored on an electronic data medium.

In many other embodiments of the present invention, after the blood treatment sessions, additional data, such as the systolic blood pressure and/or the diastolic blood pressure and/or the heart rate may be saved on an electronic data medium in addition to the at least one characteristic value for characterizing the arterial vascular stiffness.

In certain embodiments of the present invention, the historical values already stored for the at least one characteristic value from the past may form a time series, which is updated with each new value of the characteristic variable.

In addition, in many embodiments of the present invention, the device according to the invention and the method according to the invention include a statistical analysis of the historical values of the at least one characteristic value. In especially preferred embodiments, the statistical analysis is a trend. In especially preferred embodiments of the present invention, the trend can be processed graphically, for example, in the form of a curve shape in a diagram and/or as a warning on the screen and/or touchscreen of the extracorporeal blood treatment device or as a measurement chart printout from a connected printer. For the attending physician, the trend may serve as a basis for making a diagnosis with respect to the development of arterial vascular stiffness and vascular calcification.

In an especially preferred embodiment, the electronic data medium, on which the at least one value of a characteristic variable for characterizing the arterial vascular stiffness can be stored, is an individual electronic patient chip card of the particular patient. The electronic patient chip card has an electronic data memory, which is suitable and configured for reading and writing access. The special advantage of the patient chip card is that the data can be carried centrally by the patient, regardless of the blood treatment device used and the hospital visited. Furthermore, patient-specific information that enters into the calculation of the at least one characteristic value for characterizing the arterial vascular stiffness can also be saved centrally on the patient chip card. It is thus possible to access this information when the at least one characteristic variable for characterizing the arterial vascular stiffness is calculated. This always ensures that for the calculations of the at least one characteristic value for characterizing the arterial vascular stiffness, the calculation principles and assumptions are uniform in the long-term, so that the calculation results for the at least one characteristic variable for characterizing the arterial vascular stiffness are comparable to one another over a long period of time.

The concept of the electronic patient chip card comprises according to the present invention any suitable mobile electronic data medium that is or can be unambiguously assigned to one certain patient; the historical recorded values of the at least one characteristic value can be stored on this card independently of the extracorporeal blood treatment device. This also includes, for example, an SD card, memory card, memory stick, USB device and other electronic data media with which the skilled person will be familiar. In particularly preferred embodiments, the electronic data medium is an electronic patient chip card with data storage in a bank card format, in which the personal patient data can also be stored and which the patient will always carry with him together with other documents of the same format because of the practical format (personal identification, ID card, driver's license, etc.) without any additional effort.

In an especially preferred embodiment of the present invention, an extracorporeal blood treatment device, for example a hemodialysis machine, has a measurement and computation unit according to the invention, which is configured so that the at least one characteristic variable determined during the extracorporeal blood treatment is saved on the patient chip card of the particular patient.

In another especially preferred embodiment of the present invention, an extracorporeal blood treatment device, for example, has a hemodialysis machine, a measurement and computation unit according to the invention, which is configured so that the statistical analysis of the at least one characteristic value of the arterial vascular stiffness, determined during the extracorporeal blood treatment, is represented as a trend and/or as a warning on the screen of the extracorporeal blood treatment device.

According to another aspect of the invention, the at least one characteristic variable for characterizing the arterial vascular stiffness is saved in the memory of the control and computation unit of the blood treatment machine and is unambiguously assigned to the patient. It is therefore also possible to store the characteristic variable for characterizing the arterial vascular stiffness even without using the patient chip card, so that this is available further even in the case of loss or damage to the patient chip card.

According to another aspect of the present invention, the control and computation unit of the blood treatment machine is configured so that the patient-specific data stored in the memory of the control and computation unit of the blood treatment machine can be stored on a new patient chip card in the event of low or damage to the patient chip card.

Another aspect of the present invention provides that the control and computation unit of the blood treatment machine is configured so that the patient-specific data stored in the memory of the control and computation unit of the blood treatment machine can be stored on at least one computer when the dialysis machine is networked in a computer network.

The method and the measurement and computation device according to the present invention are naturally also suitable for long-term monitoring of the arterial vascular stiffness and the vascular calcification of a patient even without the link to a hemodialysis treatment. Therefore, the application of the method according to the invention and the device according to the invention is not limited to dialysis patients and is also available for healthy subjects as part of preventive measures. In many embodiments, the teaching of the present invention also includes the case in which the method according to the invention and the device according to the invention can be used independently of extracorporeal blood treatment sessions.

In conjunction with the hemodialysis treatment, however, this yields the practical advantage that the patient is regularly present in a dialysis clinic anyway, and the required measured data can be acquired without any additional effort, such as additional visits to the doctor.

EXEMPLARY EMBODIMENT

An exemplary embodiment of the device according to the invention and the method according to the invention are explained in greater detail below with reference to the figures. Additional details and advantages of the invention are described in detail on the basis of the exemplary embodiment illustrated in the figures. The reference numerals in the figures each have the same meaning consistently in all the figures.

They show.

Figure 1:
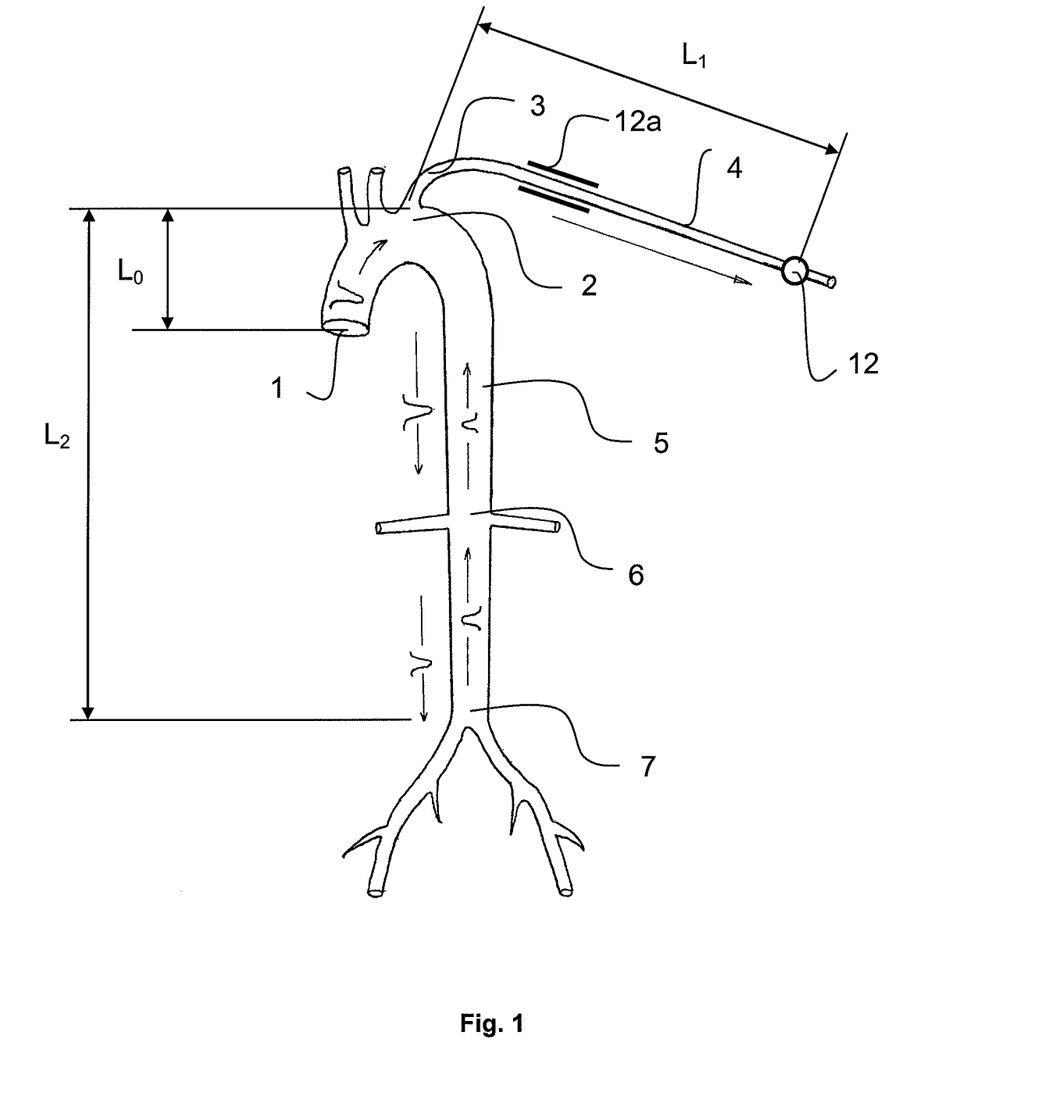
FIG. 1 a schematic diagram of the descending aorta of a person with the arteries branching off and a pressure measurement site on the person's wrist and a sphygmomanometer cuff on the person's upper arm.

FIG. 1 shows in a simplified schematic diagram the descending aorta 5 of a human patient with the largest branching arteries, namely the brachial artery 3, the renal and hepatic arteries and the iliac arteries. In the schematic diagram, the entire descending aorta 5 has the length $L_2$, which is defined as the distance between the tip of the tip of the aortic arch 2 and the aortic bifurcation 7. The aortic arch 2 with the length $L_0$ is shown schematically at the mouth 1 of the descending aorta facing the person's heart (not shown). The brachial artery 3, which develops into the radial artery 4 in the patient's arm, branches off directly from the aortic arch 2. In the schematic diagram, the brachial artery 3 and the radial artery 4 together have the length $L_1$. A pressure measurement site 12 is shown at the end of the radial artery 4 facing away from the descending aorta, a non-invasive pressure sensor optionally being attached to said pressure measuring site, for example, on the patient's wrist. An optional pressure measurement site 12a for a traditional sphygmomanometer cuff is shown at the end of the brachial artery 3 facing the descending aorta. In addition, a first branching site 6 to the renal and hepatic arteries and a second branching site representing the aortic bifurcation 7 are shown in the course of the descending aorta 5. The first branching site 6 acts as a first reflection site and the aortic bifurcation 7 acts as a second reflection site for the heart pulse wave coming from the patient's heart 1. Accordingly, reflected pressure pulse waves pass through the descending aorta 5 in the opposite direction of travel from the heart pressure pulse waves. The reflected pressure pulse waves are superimposed on the heart pressure pulse waves in the aortic arch 2 at the branch to the branch to the brachial artery 3 and pass into the brachial artery 3 and the radial artery 4 in the same direction of travel. Pressure pulse waves that can be measured at the pressure measurement site 12 on the patient's wrist and at the pressure measurement site 12a on the patient's upper arm have a characteristic shape because of the superimposed heart pressure pulse waves and reflected pressure pulse waves. The directions of travel of the pressure pulse waves are indicated with arrows in FIG. 1.

Figure 2:
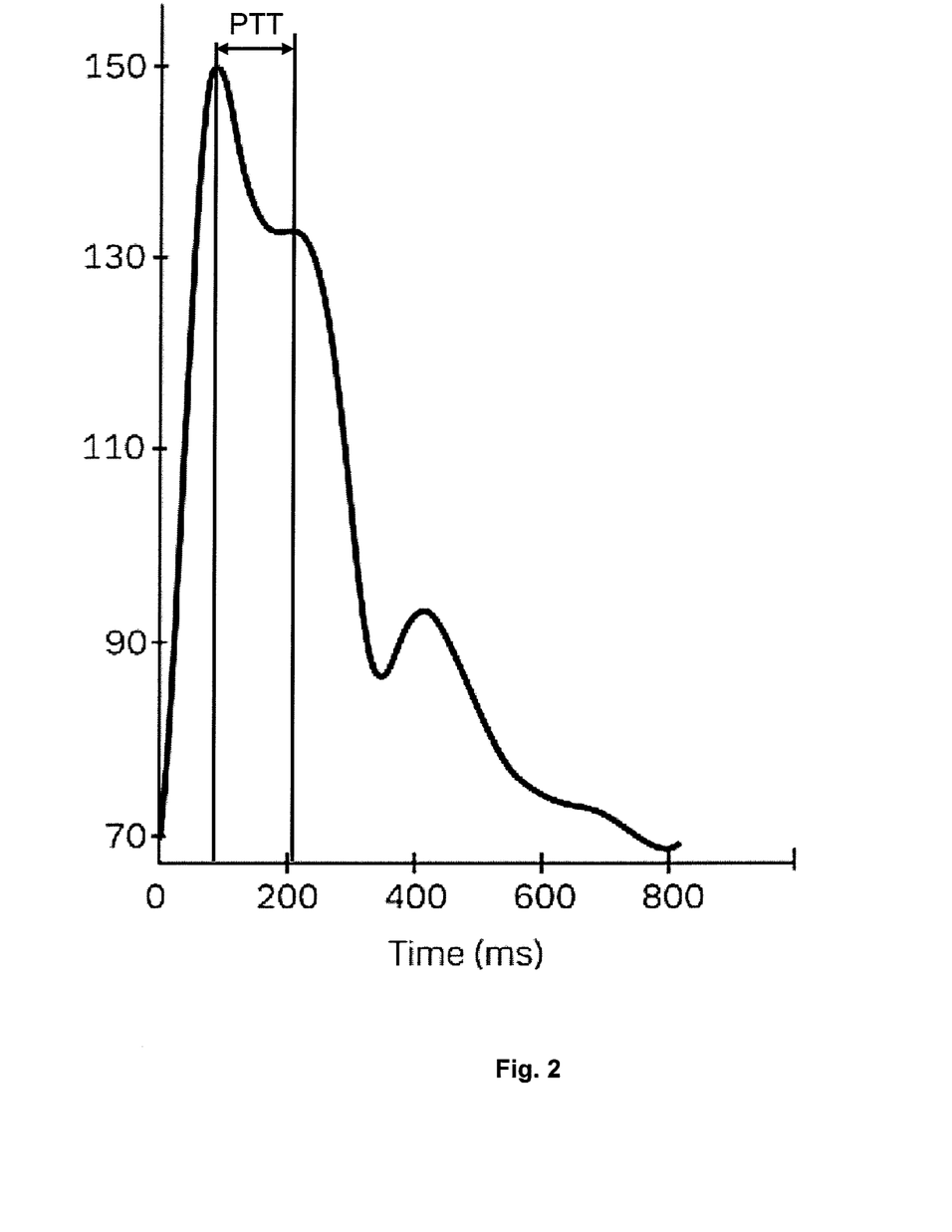
FIG. 2 an exemplary diagram of the curve of a pressure pulse wave caused by a cardiac contraction over time in a person with superimposed reflected pressure pulse waves measured at the pressure measurement site 12 on the person's wrist according to FIG. 1.

FIG. 2 shows a schematic diagram of a pressure pulse curved measured at the pressure measurement site 12 in FIG. 1 as a function of time as an example. The characteristic shape of the pressure pulse curve as a function of time has an absolute maximum at approx. $t_1=85$ ms, which occurs due to a forward directed heart pressure pulse wave and is referred to as the systolic maximum. In the subsiding phase, the pressure pulse wave reflected at the aortic bifurcation 7 is superimposed on the curve of the subsiding heart pressure pulse wave over time, so that the pressure curve over time at approx. $t_2=215$ ms has a local pulse event, for example, a turning point, as shown in FIG. 2. It is also possible that a local maximum occurs as the local pulse event instead of a turning point because of the reflected pressure pulse wave at $t_2$. In addition, another local maximum can also be discerned at approx. $t_3=410$ ms, which occurs due to the diastolic pressure pulse wave. It has been found in practice that in approx. 90% of the measurements, a local maximum occurs as a local pulse event due to the reflected pressure pulse wave at $t_2$ and in approx. 10% of the measurements a turning point occurs as a local pulse event due to the reflected pressure pulse wave at $t_2$.

The pulse wave transit time $PTT_1(L_0+L_1)$ is defined as the transit time of the pressure pulse wave caused by cardiac contraction due to the distance traveled in the aortic arch as well as in the brachial artery and the radial artery to the pressure measurement site 12 in FIG. 1.

The pulse wave transit time $PTT_2(L_0+2L_2+L_1)$ is defined as the transit time of the pressure pulse wave reflected at the aortic bifurcation due to the distance traveled in the aortic arch, in the double length of the descending aorta and in the brachial artery and in the radial artery to the pressure measurement site 12 in FIG. 1.

The pulse wave transit time in the descending aorta $PTT(2L_2)$ is defined as the transit time difference between the pressure pulse wave caused by a cardiac contraction and the pressure pulse wave reflected on the aortic bifurcation of the descending aorta due to twice the length traveled of the descending aorta. The length of the descending aorta is obtained from FIG. 1 as the measure $L_2$. The pulse wave transit time in the descending aorta PTT can be calculated as the difference between the pulse wave transit time $PTT_2$ and the pulse wave transit time $PTT_1$, as shown in equation 1.

$$PTT(2L_2)=PTT_2(L_0+2L_2+L_1)-PTT_1(L_0+L_1) \quad \text{(equation 1)}$$

Based on the principles described above, the pulse wave transit time PTT can be determined from the curve of the pressure pulse waves over time in FIG. 2, in that the transit time of the forward directed heart pressure pulse wave is subtracted from the transit time of the pressure pulse wave reflected at the second branching point ($PTT=t_2-t_1=130$ ms).

The practical calculation of the pulse wave transit time is performed by using known mathematical methods with a calculation algorithm for analysis of the curve of the measured pressure pulse waves over time, determining in particular the maximums and the turning points and calculating the measurement times of the maximums and turning points.

The calculation algorithm can be configured to perform a smoothing of the measured pressure pulse waves. The calculation algorithm may be configured to calculate the first derivations and the second derivations of the smoothed pressure pulse waves.

In addition, the calculation algorithm can be configured to extract and to analyze at least one individual pulse pressure curve from a plurality of pressure pulse curves. Analysis of the at least one pulse pressure curve may include a few, several or all of the steps mentioned below.

The calculation algorithm can be configured to detect the systolic peak at time $t_1$ and the peak of the reflection wave at time $t_2$ from the shape of the curve of an extracted pulse pressure curve.

In addition, the calculation algorithm can be configured, for example, for a plausibility check, to also detect the diastolic peak at time $t_3$ from the shape of the curve of an extracted pulse pressure curve.

The calculation algorithm can be configured to define a substitute point for the peak of the reflection wave at time $t_2$, if the analysis of the shape of the curve does not supply an unambiguous peak. The calculation algorithm can assign a turning point from the curve as a substitute point for the peak of the reflection wave at time $t_2$.

The calculation algorithm can be configured to calculate the pulse wave transit time in the descending aorta PTT as the difference between the times $t_2$ and $t_1$ ($PTT=t_2-t_1$).

The calculation algorithm can be configured to calculate the pulse wave velocity PWV of the descending aorta from the pulse wave transit time PTT of the descending aorta and the length of the descending aorta of the particular patient.

The calculation algorithm can also be configured to calculate statistical variables such as the mean value and the standard deviation of the pulse wave velocity PWV of the descending aorta and/or the pulse wave transit time PTT of the descending aorta.

The calculation algorithm for analysis of the characteristic of measured curves over time is a component of a computer program with program code, which is stored in the measurement and computation unit and prompts the machine steps of the method according to the invention, when the program code is running in the analysis unit of the measurement and computation unit.

The pulse wave velocity, which is obtained from equation 2, can be calculated using the pulse wave transit time of the descending aorta PTT($2 L_2$).

$$PWV = \frac{2 \cdot L_2}{PTT} \quad \text{(equation 2)}$$

The length $L_2$ of the descending aorta of a particular patient is determined in the present exemplary embodiment using the mathematical approach from equation 3.

$$L_2=k_{JS} \cdot L_{JS} \text{ where } 0.6 \leq k_{JS} \leq 1 \quad \text{(equation 3)}$$

In equation 3, $L_{JS}$ denotes the distance between the jugular and the pubic symphysis of the intended patient while lying down, and $k_{JS}$ denotes a correction factor, the amount of which is preferably in the range between 0.6 and 1.0. The amount of the correction factor is especially preferably 0.8. The decreasing correction factor $k_{JS}$ takes into account the fact that the theoretical distance $L_{JS}$ between the jugular and the pubic symphysis of a patient lying down is somewhat longer than the actual length of the descending aorta. The correction factor $k_{JS}$ is patient specific, but to simplify the analysis, it is possible to determine the correction factor as a mean value from empirical investigations on a representative patient population. An average value of the correction factor can be determined on the basis of angiographic MRI image data files, for example, and used as a constant in all calculations. The determination of the length $L_2$ of the descending aorta is not performed invasively.

Alternatively, the length $L_2$ of the descending aorta of a particular patient can also be calculated using the calculation method shown in equation 4.

$$L_2 = k_{JBS} \cdot L_{JBS} \text{ where } 0.8 \le k_{JBS} \le 1.2 \quad \text{(equation 4)}$$

In equation 4, $L_{JBS}$ denotes the distance between the jugular and the umbilicus of a particular patient lying down, and $k_{JBS}$ denotes a correction factor, which is obtained empirically and the value of which is preferably in the range between 0.8 and 1.2. The value of the correction is especially preferably approx. 1.0. The advantage of this alternative approach is that the attending physician can determine the correction factor $k_{JBS}$ at any time by simply measuring the length externally on the patient lying down. This alternative method of determining the length $L_2$ of the descending aorta is not performed invasively.

Again alternatively, the length $L_2$ of the descending aorta on a particular patient can also be determined using the numerical equation represented by equation 5; this length was determined by the applicant of the present patent application on the basis of investigations on a population of test subjects. In these investigations, the constants for equation 5 were found to be $\alpha = 3.10$ and $\beta = 7.00$.

$$L_2 = \alpha \cdot H - \beta \quad \text{(equation 5)}$$

In the numerical equation (equation 5), H denotes the height of the particular patient, who is standing, this height being entered into the numerical equation in units of centimeters. The length $L_2$ of the descending aorta is obtained in units of millimeters using this numerical equation. This additional alternative method of determining the length $L_2$ of the descending aorta is also not performed invasively.

It is also possible to calculate the length of the descending aorta on a particular patient by means of at least two of equations 3 to 5 and to thereby facilitate a plausibility check on the calculation results.

In the present exemplary embodiment, the length $L_2$ of the descending aorta of the particular patient is calculated by the attending physician using a non-invasive method. The result of this calculation is stored on the electronic patient chip card of the particular patient, and for performing future calculations, it can be read out from the electronic patient chip card and is then available for the calculation. By storing the length $L_2$ of the descending aorta of the particular patient on his/her individual patient chip card, it is ensured that the same value of the length $L_2$ of the descending aorta of the particular patient is always used in all calculations, independently of the clinic and the blood treatment machine, and that the results of the characteristic variable of the arterial vascular stiffness of the particular patient are comparable.

The measurement and computation unit of the present exemplary embodiment optionally combines the embodiment of the method according to the invention with a known method of continuous calculation and monitoring of the absolute and/or the relative change in the patient's blood pressure according to equation 6 for the absolute change in blood pressure and/or according to equation 7 for the relative change in blood pressure and/or according to equation 8 for the calculation of the blood pressure, either alone on the basis of the evaluation of a piezoelectric pressure measurement of the radial pulse on the patient's wrist using equation 2 for calculation of the pulse wave velocity in conjunction with one of equations 3 to 5.

$$\Delta BP(t) = m \cdot [PWV(t) - PWV(t_0)] + n \quad \text{in mmHg} \quad \text{equation (6)}$$

$$\frac{\Delta BP(t)}{BP(t_0)} = \frac{m \cdot [PWV(t) - PWV(t_0)] + n}{m \cdot PWV(t_0) + n} \quad \text{in \%} \quad \text{equation (7)}$$

$$BP(t) = m \cdot PWV(t) + n \quad \text{in mmHg} \quad \text{equation (8)}$$

In equations 6, 7 and 8, BP denotes the blood pressure in mmHg, m is a constant in units of mmHg/[m/s], n is a constant in units of mmHg, t is the time and $t_0$ is a reference point. The two constants m and n can be determined by calibration measurements for at least two different pressure states.

Through the aforementioned optional combination of joint determination of a characteristic variable for the arterial vascular stiffness and continuous measurement of the blood pressure merely by analysis of the characteristic of at least one pressure pulse wave caused by a cardiac contraction as a function of time, which requires only a single measurement point on the patient's wrist, acceptance by the user is further increased.

With the present invention, the pulse wave transit time PTT of the descending aorta and the pulse wave velocity PWV of the descending aorta can be calculated my merely analyzing the characteristic of at least one pressure pulse wave caused by a cardiac contraction and a continuous blood pressure measurement can be implemented without using additional measurement methods such as the photoplethysmogram (PPG) and electrocardiogram (ECG), so that the aforementioned practical disadvantages and acceptance problems of using such additional measurement methods as PPG and ECG are avoided as part of the continuous blood pressure measurement. This increases acceptance of the monitoring device by the user and the patient. Handling of the monitoring device is simplified and costs can be lowered. At the same time, the amount obtained for the pulse wave velocity (PWV) of the descending aorta obtained as a result of the pulse wave analysis is used as a characteristic variable for the arterial vascular stiffness and stored on the electronic patient chip card according to the invention, so that a medium-range or a long-term trend in the characteristic variable for the arterial vascular stiffness can be compiled, which can be used by the attending physician as a basis for diagnostic purposes. The trend in the arterial vascular stiffness can be used to deduce the trend in arterial vascular calcification.

Figure 3:
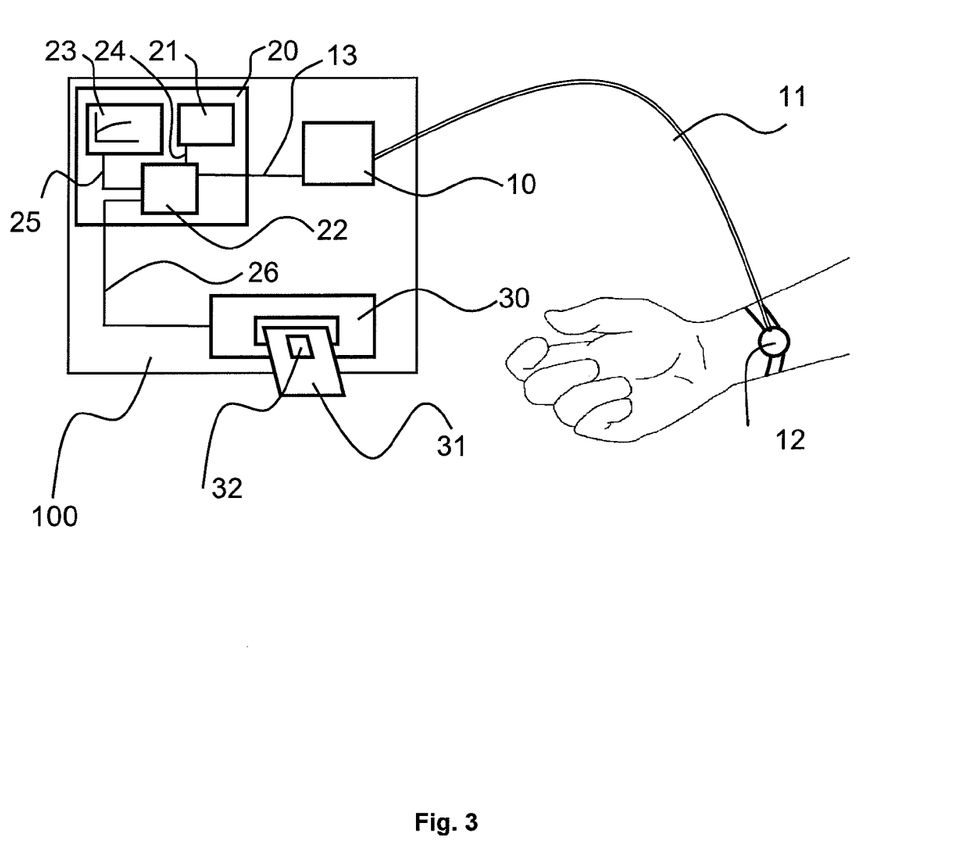
FIG. 3 a schematic diagram of the measurement and computation unit according to the invention with a pressure sensor for use at the measurement site 12 from FIG. 1.

FIG. 3 shows a schematic diagram of the measurement and computation unit 100 according to the invention in an arrangement for measuring the pressure pulse on a patient's wrist. The measuring and computation unit 100 has a pressure measuring unit 10, an analysis unit 20 and a read/write unit 30 for storing data on a patient chip card 31. The electronic patient chip card has an electronic data memory 32. The pressure measuring unit 10 is connected by a measurement//test cable 11 to a piezoelectric pressure sensor 12, which is attached to a patient's wrist in the embodiment shown here. As an alternative, wireless transmission of the pressure signal of the sensor 12 to the pressure measuring unit 10, e.g., radio-based transmission, is also possible. The analysis unit 20 has a data input unit 21, a computation and memory unit 22 and a display unit 23. The data input unit 21 is connected via a data line 24 to the computation and memory unit 22. The display unit 23 is connected to the computation and memory unit 22 via a data line 25. The computation and memory unit 22 is connected via a data line 26 to the read/write unit 30 for a patient chip card 31. The computation and memory unit 22 contains in its memory a computer program with program code for initiating the machine steps of the method according to the invention when the program code in the computation and memory unit 22 of the measurement and computation unit 100 is running.

Figure 4:
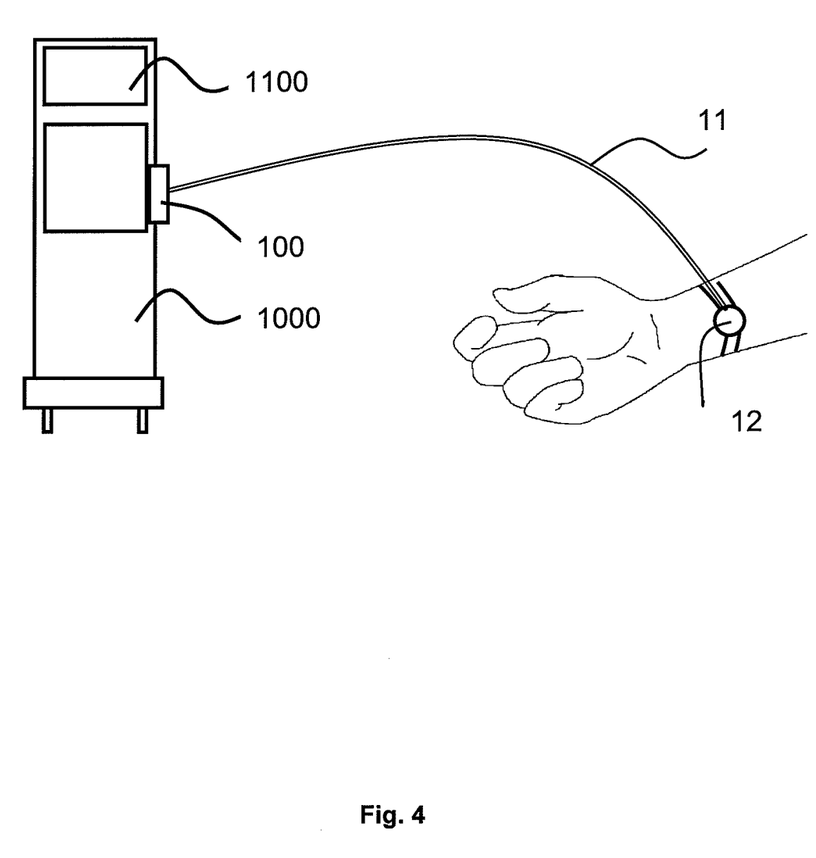
FIG. 4 a schematic diagram of the measurement and computation unit according to the invention from FIG. 3 in conjunction with an extracorporeal blood treatment machine (the extracorporeal blood circulation is not shown)

FIG. 4 shows a schematic diagram of the measurement and computation unit 100 according to the invention from FIG. 3, connected to a blood treatment machine 1000. The measuring and computation unit 100 is part of the control and computation unit of the blood treatment machine. The read and write unit for the electronic patient chip card is part of the blood treatment machine and is connected to the control and computation unit of the blood treatment machine. A touchscreen 1100 is connected to the control and computation unit. The data input unit 21 and the display unit 23 are part of the touchscreen of the blood treatment machine. The control and computation unit is configured for input of user input via the touchscreen and for display of the computation results on the touchscreen and for storing patient-related data on a particular patient, in particular the calculated values of the respective at least one characteristic value for the arterial vascular stiffness of the particular patient for the plurality of the successive measurement intervals as time series on the patient chip card 31 of the particular patient.

In the present exemplary embodiment, the attending physician uses a measuring and computation unit 100 according to one of the arrangements in FIG. 3 or in FIG. 4 and, before the start of the first interval of time, enters the value of the length of the descending aorta for the particular patient into the measuring and computation unit 100 by means of the data input unit 21. Additional data on that particular patient, such as his/her age, may also be entered. At the start of the first interval of time and at the start of each additional interval of time, the attending physician places the pressure sensor on the pressure measurement site 12 on the wrist of the particular patient and starts the measurement of at least one pressure pulse wave. The electrical measurement signal of the pressure sensor for the curve of at least one pressure pulse wave per interval of time is converted by the pressure measuring unit 10 into a pressure curve and sent to the computation and memory unit 22. A computer program with program code according to the invention runs in the computation and memory unit 22 and calculates the pulse wave velocity of the descending aorta as a characteristic variable for the arterial vascular stiffness of the particular patient, saves the values for the pulse wave velocity for all intervals of time in succession and plots the time series graphically as a trend for the particular patient in the display unit 23. Alternatively, the pulse wave transit time of the descending aorta could also be used as a characteristic variable for the arterial vascular stiffness, because the pulse wave velocity and the pulse wave transit time are inversely proportional to one another, where the length of the descending aorta is assumed to be constant according to the invention (see equation 2).

Figure 5:
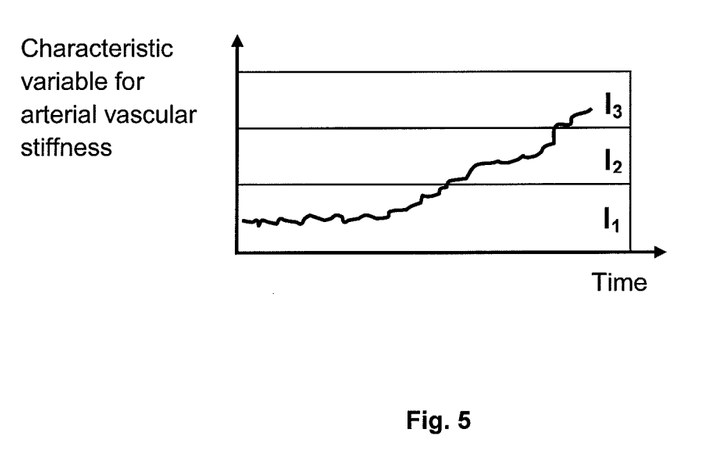
FIG. 5 a schematic diagram of an example of a trend in a characteristic variable of the arterial vascular stiffness on the display screen of the measurement and computation unit according to the invention from FIG. 3 or FIG. 4.

FIG. 5 shows schematically the graphic plot of the trend in the characteristic variable for the arterial vascular stiffness as a function of time for a display unit 23 according to FIG. 3 or FIG. 4 with predetermined value ranges $I_1$, $I_2$ and $I_3$ for the characteristic variable of the vascular stiffness, wherein $I_1$, denotes a value range of normal arterial vascular stiffness corresponding to the age of the particular patient, $I_2$ denotes a value range of increased arterial vascular stiffness and $I_3$ denotes the value range of critically elevated arterial vascular stiffness. These value ranges may be embodied in different colors in an ergonomic manner, for example, green for $I_1$ (values unremarkable), yellow for $I_2$ (warning range) and red for $I_3$ (danger range). If the trend reaches the warning range or even the danger range, this gives the attending physician an indication of the need for a control measurement and/or initiation of medical countermeasures.

Control measurements, which are not the subject matter of the present invention, may be performed by means of angiography and/or computer tomography and/or magnetic resonance tomography, for example.

The subdivision of the time axis of the graphic plot of the trend in characteristic variables for the arterial vascular stiffness may optionally represent a plurality or a multiplicity of weeks, months or years.

The time series is supplemented and updated for the particular patient after each interval of time. The updated time series forwarded by the computation and memory unit 22 to the read/write unit 30 and stored on the patient chip card 31 of the particular patient.

The measuring and computing unit 100 may include, for example, one of the two hardware arrangements described hereinafter, which for example are described using the measurements from a pressure measuring sleeve at the upper arm of a patient, however, without being limited thereto.

In a measurement via a pressure measuring sleeve at the upper arm of a patient said pressure measuring sleeve is pumped to a pressure exceeding the systolic pressure, for example to a pressure 40 mmHg above the systolic arterial blood pressure. This so-called sleeve pressure is maintained during the measuring period. During said measuring period pressure oscillations are measured. The entire amplitude of the measured pressure signal therefore comprises a portion caused by the pressure sleeve (so-called DC-portion) and an additive portion due to the pressure oscillations (so-called AC-portion). Here the amount of the portion caused by the sleeve pressure is considerably higher than the portion caused by the pressure oscillations, for example the portion due to the pressure oscillations amounts to less than 5% of the portion caused by the sleeve pressure. The portion caused by the pressure oscillations includes the desired information regarding the arterial vascular stiffness and has to be extracted from the total amplitude of the measured pressure signal.

In a first hardware arrangement the measured pressure signal is supplied to an analog high-pass filter, for example showing a limiting frequency of 0.10 Hz. Here, the DC-portion is suppressed. The filtered signal is equivalent to the AC-portion caused by the pressure oscillations and is fed to an analog low-pass filter, for example with a limiting frequency of 20 Hz. The filtered signal from the low-pass filter is amplified and supplied to an analog-digital converter (ADC) with a resolution of 12 bit and here digitized. The digital signal from the 12 bit ADC is processed according to the invention. Thus, in this hardware arrangement the measured pressure signal is first filtered and then amplified and digitized. In this first hardware arrangement signal oscillation—settling periods develop of approx. 20 seconds, which require an accordingly long measuring process with the patient. By the use of an analog high-pass filter and an analog low-pass filter the limiting frequencies are each subject to component-specific tolerances of the analog filter, which for example may range in common capacitors from 10% to 20% of the limiting frequency.

In a second hardware arrangement the measured pressure signal is first amplified and then digitized via a high-resolution analog-digital converter with a resolution of 24 bit for example. The digitized, measured pressure signal is then filtered via a digital high-pass filter, for example with a limiting frequency of 0.10 Hz and a digital low-pass filter, for example with a limiting frequency of 20 Hz, so that the AC-portion is extracted. Only then the digitized and filtered, measured pressure signal (AC-portion) is processed according to the invention. Compared to the first hardware arrangement the second hardware arrangement shows the advantage that the signal oscillation—settling periods required in the first hardware arrangement are omitted in the second hardware arrangement. This way, via the second hardware arrangement the acceptance of the measuring process by the patient to determine the vascular stiffness is further increased, because the duration of the stress upon the tissue of the upper arm due to the sleeve pressure can be reduced, since the signal oscillation—settling period is omitted. Additionally the limiting frequencies of the digital high-pass filter and the digital low-pass filter are adjustable using suitable software. Thus the problem of component-specific tolerances of the limiting frequency of the analog filter, as described for the first hardware arrangement, is not present in the second hardware arrangement. The reliability of the device according to the invention can therefore be further improved when using the second hardware arrangement.

According to the invention, the solution to the problems posed by the present invention is achieved with the exemplary embodiment presented here. However, the present invention is not limited to the exemplary embodiment.

LIST OF REFERENCE NUMERALS

| Reference numeral | Name |
| --- | --- |
| 1 | the patient's heart |
| 2 | aortic arch of the patient |
| 3 | brachial artery of the patient |
| 4 | radial artery of the patient |
| 5 | descending aorta of the patient |
| 6 | first branching point of the descending aorta |
| 7 | second branching point of the descending aorta (aortic bifurcation) |
| 10 | pressure measuring unit |
| 11 | measurement line |
| 12 | pressure measurement site on the wrist |
| 12a | pressure measurement site on the upper arm |
| 20 | analysis unit |
| 21 | data input unit |
| 22 | computation and memory unit |
| 23 | display unit |
| 30 | read/write unit |
| 31 | patient card for a particular patient |
| 100 | measurement and computation unit |
| 1000 | blood treatment machine |
| 1100 | touchscreen |

The invention claimed is:

1. A method for long-term monitoring arterial vascular stiffness of a patient comprising the steps of:
non-invasive measurement of a pressure pulse wave as a function of time, caused by a cardiac contraction of the patient, in a plurality of successive intervals of time based on at least one pressure pulse wave occurring per interval of time and corresponding to a series of successive extracorporeal blood treatment sessions of the patient or including a series of successive extracorporeal blood treatment sessions of the patient,
non-invasively determining one time the length of the descending aorta of the patient, characterized in that the length of the descending aorta of the patient ($L_2$) defined as the distance between the tip of the aortic arch and the aortic bifurcation is calculated according to at least one of the equations $$L_2 = k_{JS} \cdot L_{JS}, \text{ where } 0.6 \leq k_{JS} \leq 1,$$

wherein
$L_2$ denotes the length of the descending aorta of the patient,
$k_{JS}$ denotes a first dimensionless correction factor, and
$L_{JS}$ denotes the distance between the jugular and the pubic symphysis of the patient lying down, $$L_2 = k_{JBS} \cdot L_{JBS}, \text{ where } 0.8 \leq k_{JBS} \leq 1.2,$$

wherein
$L_2$ denotes the length of the descending aorta of the patient,
$k_{JBS}$ denotes a second dimensionless correction factor, and
$L_{JBS}$ denotes the distance between the jugular and the umbilicus of the patient, and $$L_2 = \alpha \cdot H - \beta, \text{ where } \alpha = 3.10 \text{ and } \beta = 7.00,$$

wherein
$L_2$ denotes the length of the descending aorta of the patient in mm and
H denotes the height of the patient, standing up, in cm,
storing the determined length of the descending aorta of the patient on a non-transitory computer readable medium unambiguously assigned to the patient,
evaluation of the measured pressure pulse waves as a function of time in the plurality of successive intervals of time based on the at least one pressure pulse wave per interval of time and calculating a pulse wave transit time (PTT) in the descending aorta of the patient from a smoothing of the measured pressure pulse waves as a function of time for the at least one pressure pulse wave per interval of time, wherein the pulse transit time (PTT) in the descending aorta is calculated as the difference between the time of a detected peak of the reflection wave or a detected turning point of the reflection wave in the at least one pulse pressure wave and the time of a systolic peak in the at least one pulse pressure wave,
saving the calculated pulse wave transit time for a majority of successive measurement intervals,
calculating a trend of the pulse wave transit time from the saved pulse wave transit times,
storing the trend of the pulse wave transit time as a time series on the non-transitory computer readable medium unambiguously assigned to the patient, and
monitoring the stored trend of the pulse wave transit time for a change in the pulse wave transit time indicating a change in the arterial vascular stiffness of the patient.

2. The method according to claim 1, characterized in that the first dimensionless correction factor $k_{JS}$ has a value of $0.75 \leq k_{JS} \leq 0.85$.

3. The method according to claim 1, characterized in that the pulse wave transit time is calculated under the assumption that the length is determined for the descending aorta of the patient.

4. The method according to claim 1, characterized in that the calculation of the pulse wave transit time includes a calculation of a pulse wave velocity (PWV) of the descending aorta of the patient according to the equation $$PWV = \frac{2 \cdot L_2}{PTT}$$

wherein
PWV denotes a pulse wave velocity of the descending aorta of the patient,
PTT denotes the pulse wave transit time of the descending aorta of the patient, and
$L_2$ denotes the length of the descending aorta of the patient.

5. The method according to claim 4, further comprising the step of
continuously calculating and monitoring at least one of the blood pressure of the patient in the interval of time according to the equation $$BP(t) = m \cdot PWV(t) + n,$$

the absolute change in blood pressure of the patient in the interval of time according to the equation $$\Delta BP(t) = m \cdot [PWV(t) - PWV(t_0)] + n, \text{ and}$$

the relative change in blood pressure of the patient in the interval of time according to the equation $$\frac{\Delta BP(t)}{BP(t_0)} = \frac{m \cdot [PWV(t) - PWV(t_0)] + n}{m \cdot PWV(t_0) + n},$$

wherein
BP denotes the blood pressure with a pressure unit,
m denotes a constant with a pressure unit based on a speed unit,
n denotes a constant with a pressure unit,
t denotes the time, and
$t_0$ denotes a reference point in time.

6. A measurement and computation unit, for non-invasively determining at least one characteristic variable pertaining to arterial vascular stiffness of a patient, comprising
a blood pressure measuring unit including a pressure sensor and configured for measuring pressure pulses at a measurement site on the patient's wrist or at a measurement site on the patient's upper arm and conversion into electrical pressure pulse signals,
an evaluation unit having a computation and memory unit having a computer program with program code for ordering the steps of the method according to claim 1, when the program code is running in the computation and memory unit.

7. The measuring and computation unit according to claim 6 further comprising
a data input unit for entering the length of the descending aorta of the patient or for input of data for calculating the length of the descending aorta of the patient in the computation and memory unit.

8. The measuring and computation unit according to claim 6, characterized in that the blood pressure sensor is a piezoelectric pressure pickup for non-invasive measurement of pressure pulses on the patient's wrist or a sphygmomanometer cuff for non-invasive measurement of pressure pulses on the patient's upper arm.

9. The measuring and computation unit according to claim 6 integrated into a control and computation unit of a blood treatment device for extracorporeal blood treatment or connected to a control and computation unit of a blood treatment device for extracorporeal blood treatment.

10. The measuring and computation unit according to claim 6 further comprising a read/write unit for storing the trend of the pulse wave transit time as a time series on the computer readable medium.

11. A blood treatment device for extracorporeal blood treatment in combination with the measuring and computation unit according to claim 6.

12. The blood treatment device for extracorporeal blood treatment according to claim 11 selected from the group consisting of dialysis machines, hemofiltration machines, and hemodiafiltration machines.

13. A computer program product comprising a program recorded on a non-transitory computer readable medium and coded to perform the method of claim 1 when under control of a computer running the program and incorporated in a computation and memory unit of a device comprising a blood pressure measuring unit including a pressure sensor and configured for measuring pressure pulses at a measurement site on the patient's wrist or at a measurement site on the patient's upper arm and conversion into electrical pressure pulse signals, and an evaluation unit containing the computation and memory unit.

14. The method according to claim 1, characterized in that the first dimensionless correction factor $k_{JS} = 8$.

* * * * *